(12) United States Patent
Nempont et al.

(10) Patent No.: US 11,373,361 B2
(45) Date of Patent: Jun. 28, 2022

(54) ENHANCING ULTRASOUND IMAGES

(71) Applicant: KONINKLIJKE PHILIPS N.V., Eindhoven (NL)

(72) Inventors: Olivier Pierre Nempont, Suresnes (FR); Pascal Yves Francois Cathier, Asnières-sur-Seine (FR); Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/438,229

(22) PCT Filed: Oct. 30, 2013

(86) PCT No.: PCT/IB2013/059793
§ 371 (c)(1),
(2) Date: Apr. 24, 2015

(87) PCT Pub. No.: WO2014/072890
PCT Pub. Date: May 15, 2014

(65) Prior Publication Data
US 2015/0294454 A1    Oct. 15, 2015

(30) Foreign Application Priority Data
Nov. 6, 2012   (EP) .................................... 12306368

(51) Int. Cl.
*A61B 6/00*    (2006.01)
*A61B 6/12*    (2006.01)
(Continued)

(52) U.S. Cl.
CPC ................ *G06T 15/08* (2013.01); *A61B 6/12* (2013.01); *A61B 6/4417* (2013.01); *A61B 6/469* (2013.01);
(Continued)

(58) Field of Classification Search
CPC . G06T 2207/10121; G06T 2207/10116; G06T 2207/10132; G06T 2207/10136;
(Continued)

(56) References Cited

U.S. PATENT DOCUMENTS 5,531,227 A    7/1996   Schneider
5,664,573 A    9/1997   Shmulewitz
(Continued)

FOREIGN PATENT DOCUMENTS

WO    2011070492 A1    6/2011

OTHER PUBLICATIONS

Lang et al., "US-Fluoroscopy Registration for Transcatheter Aortic Valve Implantation", Feb. 28, 2012, IEEE, Transactions on Biomedical Engineering, vol. 59, iss. 5, p. 1444-1453.*
(Continued)

*Primary Examiner* — Vincent Rudolph
*Assistant Examiner* — Timothy Choi (57) ABSTRACT

The present invention relates to image processing for enhancing ultrasound images. In order to provide image data showing the current situation, for example in a region of interest of a patient, an image processing device (10) for enhancing ultrasound images is provided that comprises an image data input unit (12), a central processing unit (14), and a display unit (16). The image data input unit is configured to provide an ultrasound image of a region of interest of an object, and to provide an X-ray image of the region of interest of the object. The central processing unit is configured to select a predetermined image area in the X-ray image, to register the ultrasound image and the X-ray image, to detect the predetermined area in the ultrasound image based on the registered selected predetermined image area, and to highlight at least a part of the detected area in the ultrasound image to generate a boosted ultrasound image.

(Continued)

The display unit is configured to provide the boosted ultrasound image as guiding information on a display area (18).

9 Claims, 7 Drawing Sheets (51) Int. Cl.
*A61B 8/00* (2006.01)
*G06T 15/08* (2011.01)
*G06T 7/30* (2017.01)
*G06T 7/62* (2017.01)
*G06T 7/70* (2017.01)
*A61B 8/08* (2006.01)
*G06T 1/00* (2006.01)

(52) U.S. Cl.
CPC .......... *A61B 6/5247* (2013.01); *A61B 8/0833* (2013.01); *A61B 8/0841* (2013.01); *A61B 8/4416* (2013.01); *A61B 8/461* (2013.01); *A61B 8/463* (2013.01); *A61B 8/469* (2013.01); *A61B 8/5261* (2013.01); *G06T 1/0007* (2013.01); *G06T 7/30* (2017.01); *G06T 7/62* (2017.01); *G06T 7/70* (2017.01); *A61B 6/4441* (2013.01); *A61B 6/487* (2013.01); *A61B 8/466* (2013.01); *G06T 2207/10121* (2013.01); *G06T 2207/10132* (2013.01); *G06T 2207/20221* (2013.01); *G06T 2207/30004* (2013.01); *G06T 2215/12* (2013.01)

(58) Field of Classification Search
CPC ....... G06T 2207/20221; G06T 2207/30; A61B 6/4417; A61B 6/4416; A61B 8/0841; A61B 8/5261; A61B 6/469
See application file for complete search history.

(56) References Cited

U.S. PATENT DOCUMENTS

| | | | |
|---|---|---|---|
| 6,006,126 A | 12/1999 | Cosman | |
| 6,019,725 A * | 2/2000 | Vesely | A61B 8/0841 128/916 |
| 6,549,802 B2 * | 4/2003 | Thornton | A61B 6/12 60/439 |
| 7,817,835 B2 | 10/2010 | Fan et al. | |
| 8,131,041 B2 | 3/2012 | Maarten | |
| 9,237,929 B2 | 1/2016 | Olivier et al. | |
| 9,521,994 B2 | 12/2016 | Kamen et al. | |
| 2002/0193677 A1 | 12/2002 | Thornton | |
| 2005/0171428 A1 | 8/2005 | Fichtinger et al. | |
| 2006/0237652 A1 | 10/2006 | Kimohy et al. | |
| 2007/0247454 A1 * | 10/2007 | Rahn | A61B 6/5247 345/419 |
| 2007/0276243 A1 * | 11/2007 | Gerard | A61B 6/12 600/440 |
| 2008/0146919 A1 | 6/2008 | Camus et al. | |
| 2008/0199059 A1 | 8/2008 | Eck et al. | |
| 2008/0283771 A1 | 11/2008 | Li | |
| 2009/0088628 A1 | 4/2009 | Klingenbeck-Regn | |
| 2010/0063400 A1 * | 3/2010 | Hall | A61B 8/0841 600/466 |
| 2010/0129963 A1 | 5/2010 | Chen et al. | |
| 2010/0228076 A1 | 9/2010 | Blank et al. | |
| 2011/0190633 A1 | 8/2011 | Kawagishi et al. | |
| 2012/0245458 A1 | 9/2012 | Gogin et al. | |

OTHER PUBLICATIONS

Gao et al., "Registration of 3D trans-esophageal echocardiography to X-ray fluoroscopy using image-based probe tracking", May 12, 2011, Elsevier, Medical Image Analysis 16, p. 38-49.*

Su et al., "Prostate brachytherapy seed localization by analysis of multiple projections: Identifying and addressing the seed overlap problem", May 2004, Am. Assoc. Phys. Med, Medical Physics vol. 31, iss. 5, p. 1277-1287. (Year: 2004).*

Wu et al., "Real-Time Catheter Extraction from 2D X-Ray Fluoroscopic and 3D Echocardiographic Images for Cardiac Interventions" , Oct. 2012, Springer, Statistical Atlases and Computational Models of the Heart. Imaging and Modelling Challenges: Third International Workshop, STACOM 2012, p. 198-206. (Year: 2012).*

Sadeghi, N.A. et al. "CT-Enhanced Ultrasound Image of a Totally Deflated Lung for Image-Guided Minimally Invasive Tumor Ablative Procedures", IEEE Transactions on Biomedical Engineering, IEEE Service Center, Piscataway, NJ, vol. 57, No. 10, Oct. 2, 2010, pp. 2627-2630.

* cited by examiner

ENHANCING ULTRASOUND IMAGES

CROSS-REFERENCE TO PRIOR APPLICATIONS

This application is the U.S. National Phase application under 35 U.S.C. § 371 of International Application Serial No. PCT/IB2013/059793, filed on Oct. 30, 2013, which claims the benefit of EP Application No. 12306368.7, filed on Nov. 6, 2012. These applications are hereby incorporated by reference herein.

FIELD OF THE INVENTION

The present invention relates to an image processing device for enhancing ultrasound images, to a medical imaging system, and to a method for enhancing ultrasound images, as well as to a computer program element and to a computer-readable medium.

BACKGROUND OF THE INVENTION

In medical examinations, such as endovascular interventions, different types of medical imaging can be used, for example the positioning of a mitral clip is performed under fluoroscopic X-ray imaging and ultrasound imaging for guidance purposes. The X-ray images are used for visualizing tools, such as catheters, clips, or the like, and also bone structures, whereas ultrasound imaging can be used for visualizing soft tissues. WO 2011/070492 A1 describes the combination of ultrasound image data and X-ray image data. An ultrasound probe is detected in the X-ray image, and acquisition settings of the ultrasound probe are visualized within the X-ray image. It has been shown that ultrasound images allow the visualization of soft tissues, which becomes increasingly important in the developing field of minimally invasive interventions. However, it has also been shown that providing fluoroscopic images and ultrasound images next to each other requires attention and awareness of the user mentally combining the two different contents shown in the respective images.

SUMMARY OF THE INVENTION

There may thus be a need to provide image data showing the current situation, for example in a region of interest of a patient, wherein the image data requires reduced and minimum interpretation and combination skill on the side of the user.

The object of the present invention is solved by the subject-matter of the independent claims, wherein further embodiments are incorporated in the dependent claims. It should be noted that the following described aspects of the invention apply also for the image processing device for enhancing ultrasound images, for medical imaging system, and for the method for enhancing ultrasound images, as well as for the computer program element and for the computer-readable medium.

According to a first aspect of the present invention, an image processing for enhancing ultrasound images is provided, comprising an image data input unit, a central processing unit, and a display unit. The image data input unit is configured to provide an ultrasound image of a region of interest of an object, and to provide an X-ray image of the region of interest of the object. The central processing unit is configured to select a predetermined image area in the X-ray image. The central processing unit is further configured to register the ultrasound image and the X-ray image, and to detect the predetermined area in the ultrasound image based on the registered selected predetermined image area. The central processing unit is further configured to highlight at least a part of the detected area in the ultrasound image to generate a boosted ultrasound image. Thus, the term "boosted" or "boosting" in the invention refers to an improvement for a user in the visibility of an object. The display unit is configured to provide the boosted ultrasound image as guiding information on a display area.

The term "register" refers to providing a positional or spatial relation between the X-ray image and the ultrasound image.

According to a second aspect, a medical imaging system is provided, comprising an ultrasound imaging device, an X-ray imaging device, and an image processing device. The image processing device is provided according to the above mentioned example, or examples mentioned below. The ultrasound imaging device is configured to acquire and provide an ultrasound image of a region of interest of an object, and the X-ray imaging device is configured to acquire and provide an X-ray image of the region of interest of the object.

According to a third aspect, a method for enhancing ultrasound images is provided, comprising the following steps:
a) providing an ultrasound image of a region of interest of an object;
b) providing an X-ray image of the region of interest of the object;
c) selecting a predetermined image area in the X-ray image;
d) registering the ultrasound image and the X-ray image;
e) detecting the predetermined image area in the ultrasound image based on the registered selected predetermined image area; and
f) highlighting at least a part of the detected predetermined image area in the ultrasound image to generate a boosted ultrasound image.

By selecting the predetermined image area in the X-ray image, and by detecting the predetermined image area in the ultrasound image based on the registration, it is possible to enhance an ultrasound image based on information that is available in the X-ray image. Thus, image content, or image information, of the X-ray image is transferred to the ultrasound image. This provides image information that can be provided to the user, which image information is presented in one image, thus facilitating the viewing and understanding process of the provided image information.

According to an exemplary embodiment, the central processing unit is configured to project the selected area into the ultrasound image, and to detect the predetermined area in the ultrasound image based on the projected area.

In an example, the projection is a "back-projection". The X-ray image may be a projection of the 3D world. In case of outlining an object in the X-ray image, it is possible to use back-projection to refer to the largest volume in 3D whose projection is that outline.

According to an exemplary embodiment, the central processing unit is configured to detect at least one target object in the X-ray image, for example an interventional tool or device. The central processing unit is further configured to detect the at least one target object in the ultrasound image based on the registered target object. The central processing unit is further configured to highlight an area of the detected target object in the ultrasound image.

According to an exemplary embodiment, the central processing unit is configured to register the selected area as an outline, and to select objects in the ultrasound image that fit into the projected outline.

The registration may be provided as projection or back-projection.

According to an exemplary embodiment, the ultrasound imaging device comprises a probe that is used for acquiring the ultrasound image, and a registration unit is provided, which is configured to register the ultrasound probe in the X-ray image.

According to an exemplary embodiment, the X-ray imaging device and the ultrasound imaging device are configured to acquire the images simultaneously.

According to an exemplary embodiment, the ultrasound image device is configured to a first sequence of ultrasound images, and the X-ray imaging device is configured to acquire a second sequence of X-ray images.

For example, the central processing unit is configured to detect the predetermined image area in one of the X-ray images and to track the predetermined image area in the other X-ray images. Further, the central processing unit is configured to register the first sequence of ultrasound images with the second sequence of X-ray images. The central processing unit is further configured to detect the predetermined image area in the first sequence of ultrasound images based on the registered selective predetermined image area. Further, the central processing unit is configured to highlight the area of the detected predetermined image area in the first sequence of ultrasound images.

According to an aspect, the present invention proposes to boost an image by improving the visualization of ultrasound images or ultrasound 3D volumes. Such a boosting may be obtained by enhancing, for example colorizing, target objects, such as catheters, prosthesis, clips or the like, which can easily be detected and tracked in a fluoroscopy. Alternatively such a boosting may be obtained by outlining these target objects. As mentioned above, for example in case of endovascular interventions, X-ray images, such as fluoroscopic images allow a good visualization of endovascular tools, but it does not allow a visualization of soft tissue (without the use of contrast agent) or a 3D visualization. Ultrasound allows a 2D or 3D visualization including soft tissues. However the contrast between tools and soft tissues is very low. Further, in two-dimensional ultrasound images, only a part of a tool may be visible. Therefore the interpretation of such image is not straight forward. The present invention proposes to perform the detection, or the selection, of target objects, or other predetermined image area in fluoroscopic images, in which they are properly contrasted. Further, the target objects may be tracked in the X-ray images. Based on a registration, for example a live registration, of ultrasound images and X-ray images, the target objects, or predetermined image areas can be detected in the ultrasound image, and the target objects can be enhanced in the ultrasound images, for example by colorizing them. It must be noted that the X-ray image data is only used to detect in the ultrasound images target objects or predetermined image area whose detection could be very challenging otherwise. Indeed the high contrast of interventional tools in X-ray images makes easier their detection and tracking. Even if in ultrasound images they are poorly contrasted (with respect to soft tissues), their detection is facilitated by the position and shape priors that arise from the X-Ray detection and that are based on the registration of the two image modalities. Instead of combining the two images, the transfer from the X-ray image to the ultrasound image is provided for detection and/or positioning purposes only. However, the transfer of the positioning data from the X-ray image to the ultrasound image is adding further information to the ultrasound image, which information can not be retrieved from the original ultrasound image itself.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings:

FIG. 7 shows photographic images of FIG. 6, i.e. FIG. 7a shows the content of FIG. 6a, and FIG. 7b shows the content of FIG. 6b.

DETAILED DESCRIPTION OF EMBODIMENTS

Figure 1:
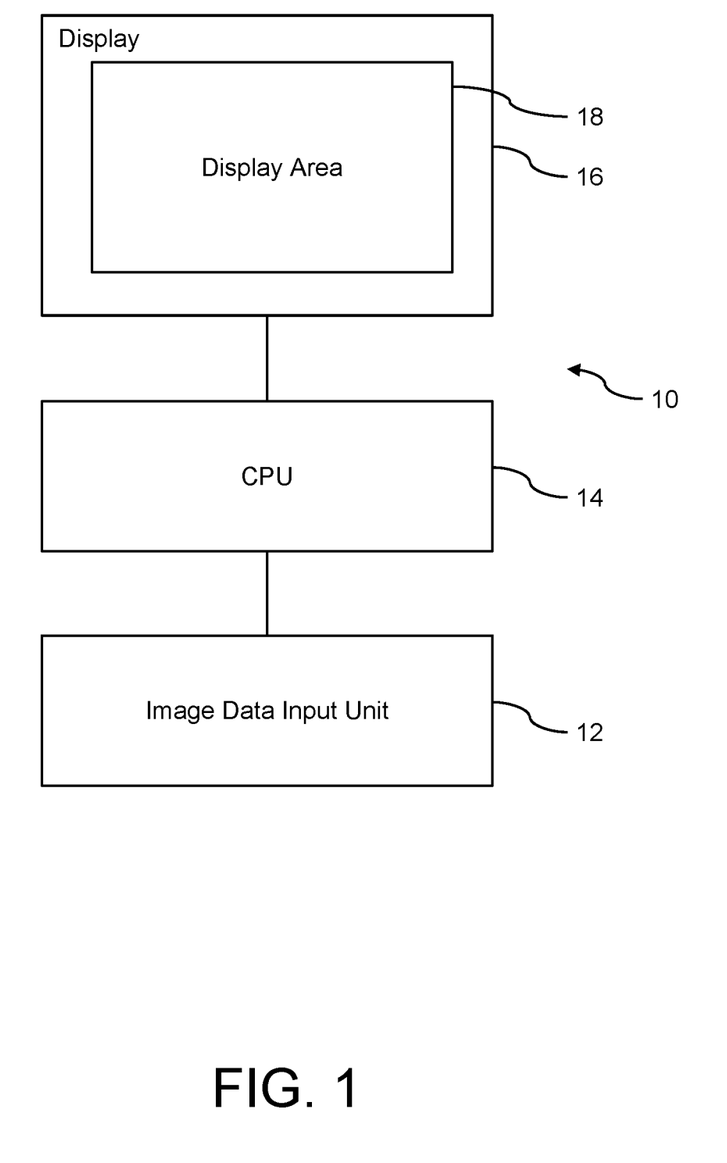
FIG. 1 shows an example of an image processing device in a schematic setup.

FIG. 1 shows an image processing device 10 for enhancing ultrasound images, comprising an image data input unit 12, a central processing unit 14, and a display unit 16. The image data input unit 12 is configured to provide an ultrasound image of a region of interest of an object, and to provide an X-ray image of the region of interest of the object.

The central processing unit 14 is configured to select a predetermined image area in the X-ray image, to register the ultrasound image and the X-ray image, to detect the predetermined area in the ultrasound image based on the registered selected predetermined image area, and to highlight at least a part of the detected area in the ultrasound image to generate a boosted ultrasound image. The display unit is configured to provide the boosted ultrasound image as guiding information on a display area 18.

In a further example (not further shown), the central processing unit is configured to project the selected area into the ultrasound image, and to detect the predetermined area in the ultrasound image based on the projected area.

In a further example (also not further shown), the central processing unit is configured to detect at least one target object in the X-ray image, and to detect the at least one target object in the ultrasound image, based on the registered target object, and to highlight an area of the detected target object in the ultrasound image.

In an example, the central processing unit 14 is configured to project the at least one detected target object into the ultrasound image, and to detect the at least one target object in the ultrasound image based on the projected target object.

In a further example (not shown in detail), the central processing unit 14 is configured to register the selected area as an outline, in 2D as well as in 3D, and to select objects in the ultrasound image that fit into the projected outline.

Figure 2:
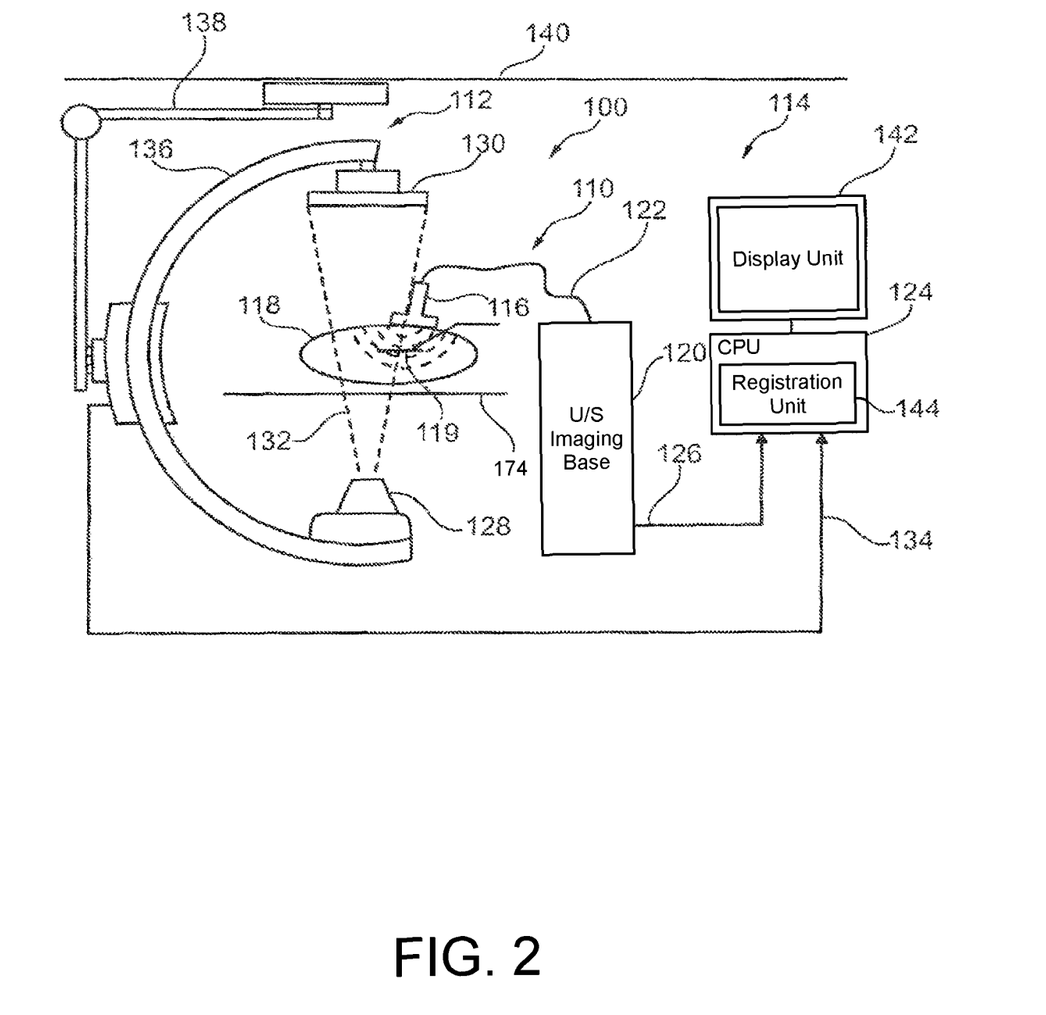
FIG. 2 shows an example of a medical imaging system with an ultrasound imaging device and an X-ray imaging device.

FIG. 2 shows a medical imaging system 100, comprising an ultrasound imaging device 110, and an X-ray imaging device 112. Further, an image processing device 114 is provided, according to the example shown in FIG. 1, or according to examples described above and below. The ultrasound imaging device 110 is configured to acquire and provide an ultrasound image of a region of interest of an object, and the X-ray imaging device 112 is configured to acquire and provide an X-ray image of the region of interest of the object.

For example, the ultrasound imaging device 110 comprises a transducer 116, which may be brought into contact with an object 118. An interventional tool 119 may be present. In another example, instead of the tool, another target object or other predetermined image area are provided. For example, to bring the transducer 116 into contact with the object 118 can be done manually, or also in a motor-driven way. The, for example handheld, transducer 116 is connected to an ultrasound imaging base 120, which connection is indicated by a line 122, but which can of course also be provided wireless. The ultrasound imaging base 120 is connected to a central processing unit 124, as indicated by connecting arrow 126. This may be a wire connection or a wireless connection. The transducer 116 acquires ultrasound image information of the region of interest of the object 118.

The X-ray imaging device 112 comprises an X-ray source 128, and an X-ray detector 130. The X-ray source 128 provides X-ray radiation 132 towards the detector 130, thereby passing the object 118, in order to provide X-ray image information. The X-ray imaging device 112 is connected to the central processing unit 124 by a connecting arrow 134. Once again, this schematically shown connection may be provided wireless or wire-based.

For example, the X-ray imaging device 112 is provided as a C-arm arrangement, where the X-ray source 128 and the X-ray detector 130 are provided on opposing ends of the a C-arm 136, which may be supported by a ceiling support 138, suspended from a ceiling 140. Of course, also other X-ray imaging device types can be used, for example mounted to the floor, or mobile X-ray imaging devices, for example mobile C-arm devices, or other standing X-ray imaging devices with non-movable X-ray source and X-ray detector.

The central processing unit 124 is thus formed integrally with a not further shown image data input unit to receive ultrasound images, or ultrasound image data from the ultrasound imaging device 110 and X-ray images, or X-ray image data, from the X-ray imaging device 112. The central processing unit 124 is further connected to a display unit 142.

The control processing unit 124 has also been described above in relation with FIG. 1, i.e. the central processing unit has reference numbers 14 and 124. Thus, it is referred to the above for the configuration of the central processing unit 124 of FIG. 2. Similar applies for the display unit, which is given the reference numeral 142 in FIG. 2 and reference numeral 16 in FIG. 1. Thus, it is also referred to the description relating to FIG. 1 with respect to the display unit. The object 118 may be a patient provided on an object support 174, for example a patient table.

According to an example, as shown in FIG. 2, but not meaning a necessary feature of FIG. 2, the ultrasound imaging device comprises a probe, for example the transducer 116. The probe is used for acquiring the ultrasound image. Further, a registration unit 144 is provided, for example integrated with the central processing unit 124. However, the registration unit 144, also shown in FIG. 2, does not mean that this is a necessary component of the medical imaging system 100. The registration unit 144 is provided and configured to register the ultrasound probe 116 in the X-ray image.

According to a further example, the X-ray imaging device 112 and the ultrasound imaging device 110 are configured to acquire the images simultaneously.

According to a further example (not further shown in detail), the ultrasound image device 110 is configured to acquire a first sequence of ultrasound images, and the X-ray imaging device 112 is configured to acquire a second sequence of X-ray images.

According to a further example, the imaging processing device 114 is configured to perform the examples and methods as described below.

Figure 3:
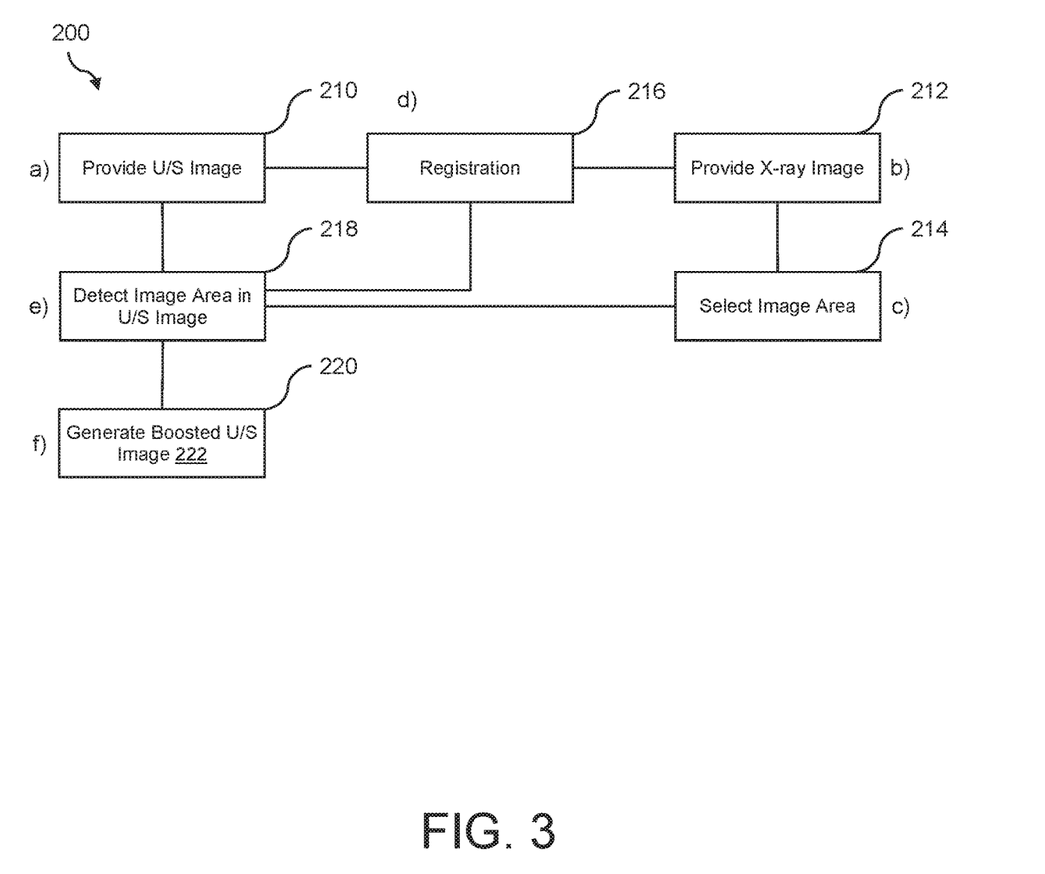
FIG. 3 shows an example of basic steps of a method for enhancing ultrasound images.

FIG. 3 shows a method 200 for enhancing ultrasound images, where the following steps are provided. In a first provision step 210, an ultrasound image of a region of interest of an object is provided. In a second provision step 212, an X-ray image of the region of interest of the object is provided. In a selecting step 214, a predetermined image area is selected in the X-ray image. Further, in a registration step 216, the ultrasound image and the X-ray image are registered. Next, in a detection step 218, the predetermined image area in the ultrasound image is detected based on the selected predetermined image area and on the registration. Finally, a highlighting step 220 is provided, in which at least a part of the detected predetermined image area in the ultrasound image is highlighted to generate a boosted ultrasound image 222.

The first provision step 210 is also referred to as step a), the second provision step 212 as step b), the selecting step 214 as step c), the registration step 216 as step d), the detection step 218 as step e), and the highlighting step 220 as step f).

The order of the steps, in particular of steps a), b), and c), is not mandatory, except that the X-ray image and the ultrasound image are registered in step d) before the selected area is detected in the ultrasound image in step e).

In an example, between step d) and e), the following step is provided: d/e) projecting the selected area into the ultrasound image, wherein in step e), the predetermined area is detected in the ultrasound image, based on the projected area.

The ultrasound image data can be 2D image data or 3D image data.

According to a further example (not shown in detail), step c) comprises detecting at least one target object in the X-ray image. In other words, the predetermined image area is a target object, such as an interventional device or other objects inside a patient. Step d) comprises registering at least one detected target object in the ultrasound image. Thus, the target position information achieved from the X-ray image is transferred by a registration to the ultrasound image. Step e) comprises detecting the at least one target object in the ultrasound image based on the target image area in X-ray and on the registration. Step f) comprises highlighting a part of an area of the detected target object in the ultrasound image. In relation with the term "registered target object", it is noted that the outline in X-ray is done in projective geometry whereas the US is in the 3D world. Based on the outline in X-ray it is possible to define some prior, but it's not possible to get directly a 3D object.

In an example, step d/e) comprises projecting the at least one detected target object into the ultrasound image, wherein step e) comprises detecting the at least one target object in the ultrasound image based on the projected target object.

According to a further example (not further shown in detail), the predetermined image area is an interventional tool, which is detected and tracked automatically for the selecting step in step c).

In an example, a step g) is provided, in which the boosted ultrasound image is provided as guiding information on a display.

In a further example, in step d), the selected area is projected as an outline, and in step e), objects are selected in the ultrasound image that fit into the projected outline.

In one example, the images provided in step a) and b) are acquired simultaneously, as already indicated above.

The predetermined image area, or target object, may be an interventional tool, such as a catheter, prosthesis, clip, and the like. For example, the generated boosted ultrasound image may be a tool-boosted ultrasound image. The highlighting may be provided as colorizing the detected area in the ultrasound image to differentiate predetermined image areas and other structures.

For example registering in step d), an ultrasound probe used for acquiring the ultrasound image is registered in the X-ray image.

The projecting step is provided as a back-projection.

Figure 4:
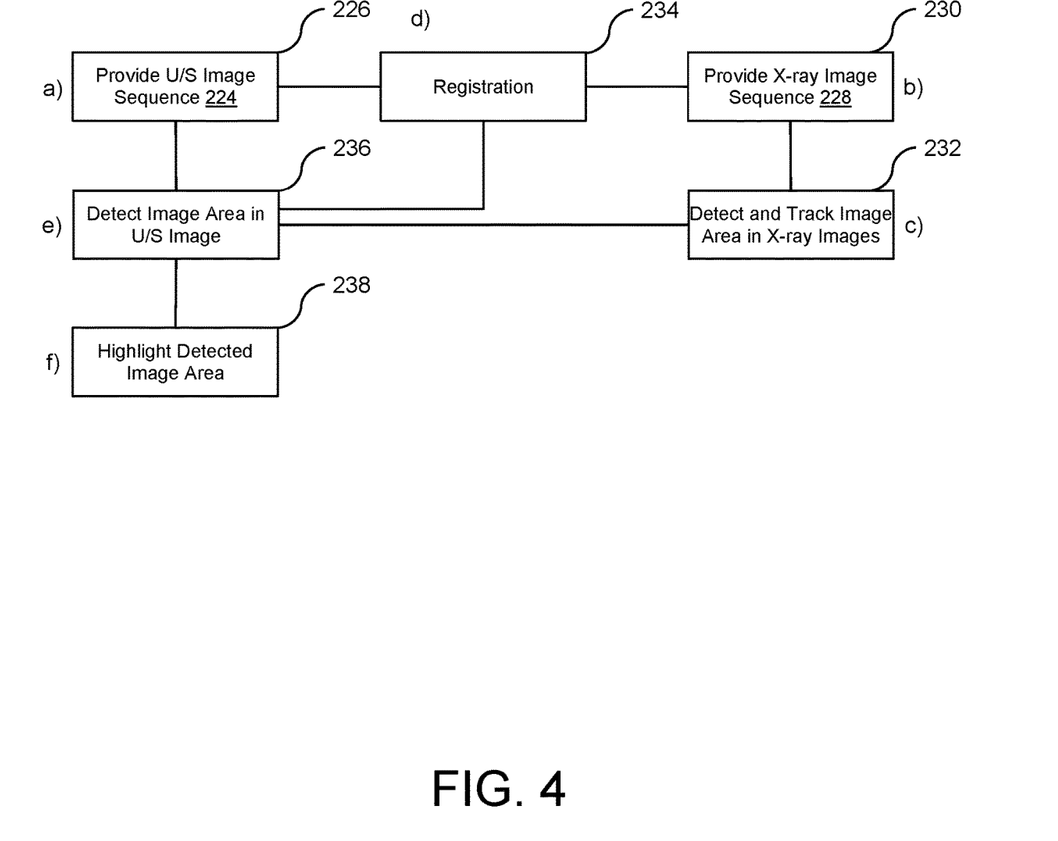
FIG. 4 shows a further example of a method for enhancing ultrasound images.

FIG. 4 shows a further example, wherein in step a), a first sequence of ultrasound images 224 of the region of interest is provided in a first provision step 226. In step b), a second sequence of X-ray images 228 of the region of interest is provided in a second provision step 230. In step c), the predetermined image area is detected in a detection step 232 in one of the X-ray images and tracked in the other X-ray images. In step d), a registration step 234 is provided, where the first sequence of ultrasound images is registered with the second sequence of X-ray images. In step e), the predetermined image area is detected in the first sequence of ultrasound images based in a detection step 236, based on the registered selected predetermined image area. Further, in step f), the area of the detected predetermined image area is highlighted in a highlighting step 238 in the first sequence of ultrasound images.

In one example, in step c), the at least one target object is detected in one of the X-ray images and tracked in the other X-ray images. In step e), the target object is detected in the first sequence of ultrasound images based on the registered selected predetermined image area, and in step f), the at least one target object is detected in the first sequence of ultrasound images, and in step g), the area of the detected target object is highlighted in the first sequence of ultrasound images.

In another example, in step e), the target object is projected in the first sequence of the ultrasound images, and in step f), the at least one target object is detected in the first sequence of ultrasound images.

The X-ray image may be provided as fluoroscopic image data. In one example, the target objects are automatically detected. In another example, the target objects are manually detected.

In a further example, a method for operating an image processing apparatus is provided, wherein image data processing steps of the preceding examples are provided.

Figure 5:
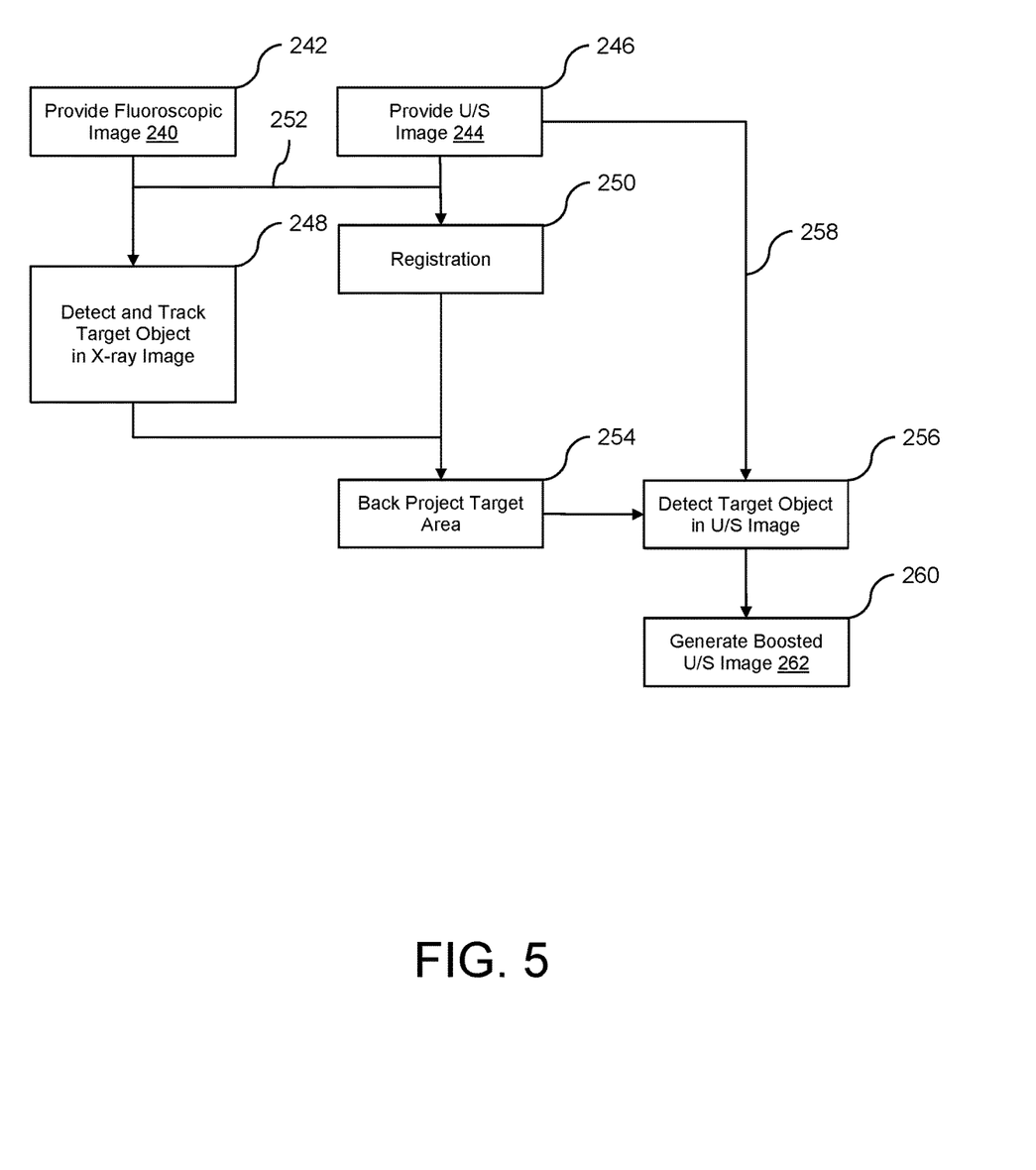
FIG. 5 shows a further example of a method for enhancing ultrasound images.

FIG. 5 shows a further example of a method, where fluoroscopic image(s) 240 is (are) provided in a first provision step 242. Further, for example simultaneously, ultrasound image(s) 244 is (are) provided in a second provision step 246. Next, in a detection step 248, target objects in the X-ray image(s) 240 are detected and tracked. Next, a registration step 250 is provided, in which the ultrasound image(s) 244 and the fluoroscopic image(s) 240 are registered. An arrow 252 indicates the connecting of the two image worlds by the registration 250. The information from the registration 250, together with the result from the detecting and tracking step 248 is then used in a back-projection step 254. The latter is then used in a detection step 256, in which the target objects are detected within the ultrasound image(s), provided from the second provision step 246, which provision of the ultrasound image data is indicated with an arrow 258. Upon the detection step 256, an enhancement of the ultrasound image is provided, for example by computing a colorized ultrasound image in a computation step 260.

For example, if the target object(s) is an endovascular interventional device, or other device, also referred to as a tool, a boosted ultrasound image 262 is provided as guiding information, for example on a display area of the display unit. Thus, a boosting of tools in ultrasound images is provided, based on the detection in fluoroscopic images.

For example, the fluoroscopic image data 240 and the ultrasound image data 244 are acquired in a simultaneous performance, and both live streams are available. In the detection/tracking of the target object in the X-ray image, the target objects are either manually selected or automatically detected in one X-ray frame. It is possible to select all radio-opaque objects, or just one target object, such as a clip. Then, the position of the selected objects is tracked in the next frames. In the registration step, the ultrasound acquisition and the X-ray acquisition are registered. This task may be achieved by registering the ultrasound probe when it is visible in the fluoroscopic image. In the back-projection, the outline of detected objects (in X-ray frames) is back-projected, for example, onto the 2D ultrasound images or within the 3D ultrasound volumes. In the 2D case, it is possible to obtain also 2D outlines where the target objects can be (if it lies in the ultrasound plane). In the 3D case, it is possible to obtain beams along the outline. In the detection 256 of the target objects within the ultrasound image, it is provided to select in the ultrasound image objects that fit into the back-projected outlines, for example. In the computation step 260, colorizing ultrasound image data, the ultrasound image is colorized to differentiate the target objects in the other structures, such as soft tissues. Instead of colorizing, other means of highlighting or emphasizing the respective areas are provided. Other dedicated renderings are also possible, for instance acting on the transparency in 3D image data.

Figure 6A:
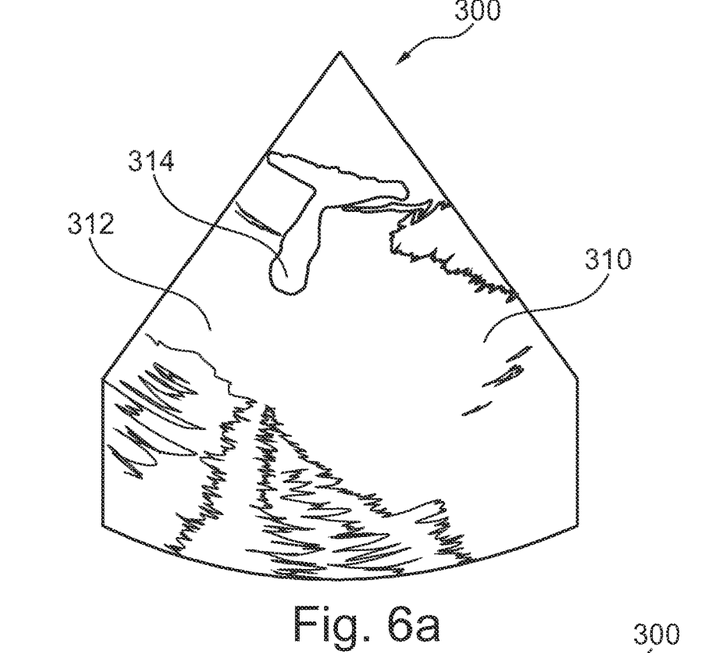
FIG. 6 shows an example of a boosted ultrasound image as a 2D echogram in FIG. 6a and as a 3D echogram in FIG. 6b as a line drawing.
Figure 6B:
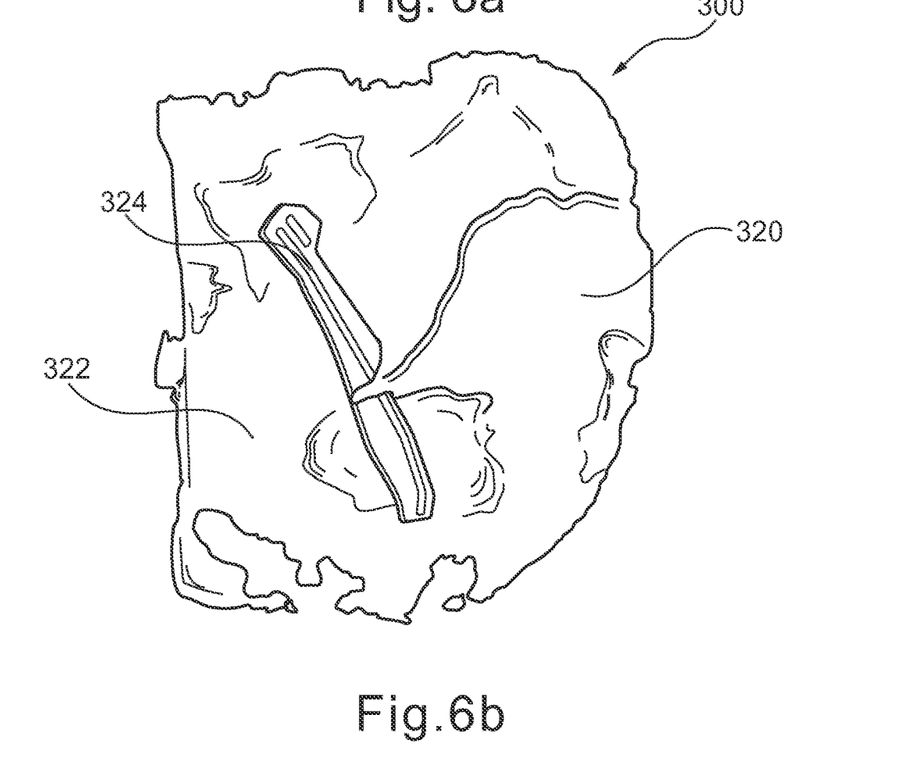

FIG. 6 shows an example of a boosted ultrasound image 300 as a 2D echogram 310 in FIG. 6a and as a 3D echogram 320 in FIG. 6b.

In FIG. 6a an echogram illustration 312 is shown with a highlighted area 314, for example relating to a region of a device, wherein the device has been detected in an X-ray image as described above. The highlighted area may be coloured or contrast enhanced etc.

In FIG. 6b an echogram illustration 322 is shown with a highlighted area 324, for example relating to a region of a device, wherein the device has been detected in an X-ray image as described above. The highlighted area may be coloured or contrast enhanced etc.

Figure 7A:
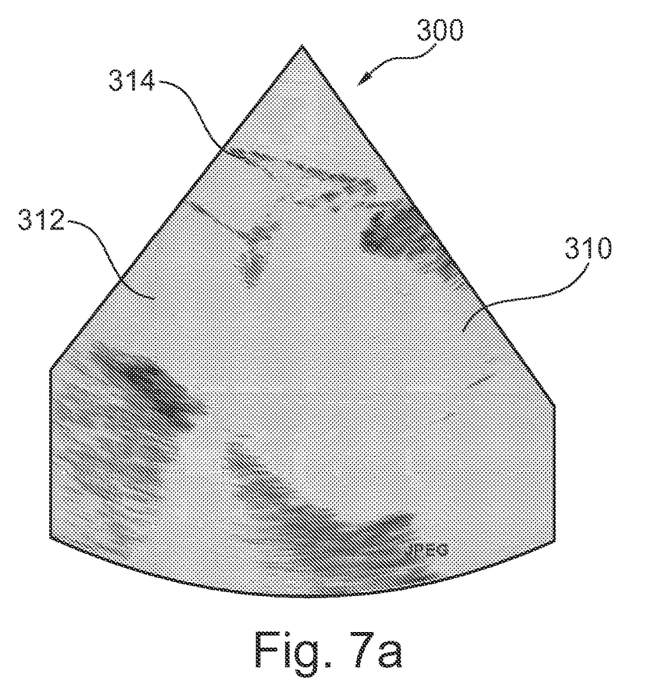
Figure 7B:
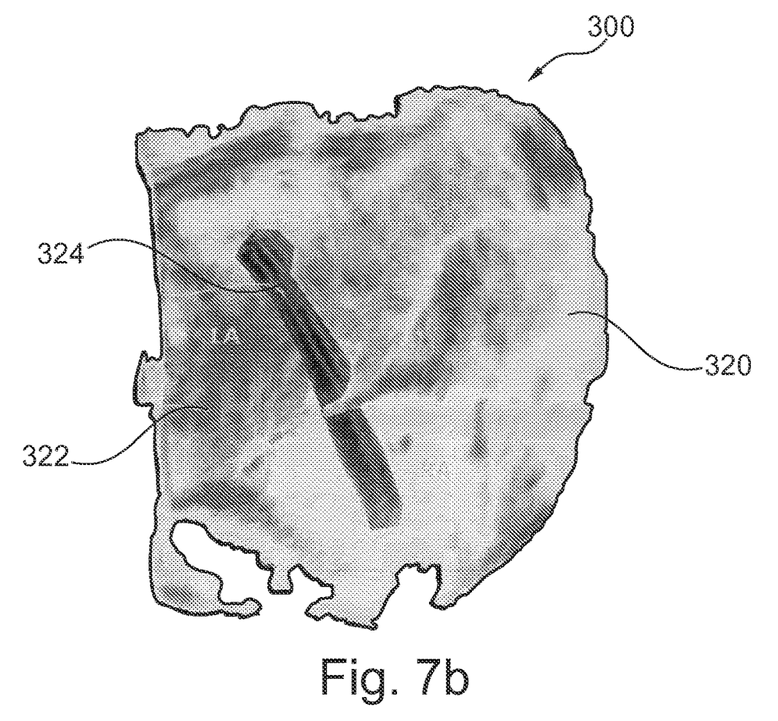

FIG. 7 shows a respective photographic illustration of FIG. 6, i.e. FIG. 7a shows the content of FIG. 6a, and FIG. 7b shows the content of FIG. 6b. Thus, same reference numerals are used.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing device for enhancing ultrasound images for a medical procedure, comprising:
   a processor configured to:
      receive a plurality of ultrasound images of a region of interest of an object and a plurality of X-ray images of the region of interest of the object;
      select at least one target object in one X-ray image of the plurality of X-ray images, wherein the at least one target object is an interventional tool configured to be moved in the region of interest of a patient during the medical procedure;
      track movement of the at least one target object in other X-ray images of the plurality of X-ray images subsequent to the one X-ray image;
      register the plurality of ultrasound images and the plurality of X-ray images;
      detect the at least one target object in the plurality of ultrasound images based on a tracking of movement of the at least one target object and the registration, wherein the detection by the processor comprises: i) projecting an outline of the at least one target object in the plurality of X-ray images into the plurality of ultrasound images and ii) detecting the at least one target object in the plurality of ultrasound images based on selecting at least one object in the plurality of ultrasound images that fit into the projected outline;
      generate a boosted ultrasound image in which at least an area of the detected at least one target object in the plurality of ultrasound images is highlighted to track movement of the at least one target object in the region of interest of the patient during the medical procedure; and
   a display configured to present the boosted ultrasound image as guiding information on a display area.

2. A medical imaging system, comprising:
   the image processing device according to claim 1;
   an ultrasound imaging device configured to acquire and provide the plurality of ultrasound images of the region of interest of the object; and
   an X-ray imaging device configured to acquire and provide the plurality of X-ray images of the region of interest of the object.

3. The system according to claim 2, wherein the ultrasound imaging device comprises an ultrasound probe that is used for acquiring the plurality of ultrasound images; and
   wherein the processor is further configured to register the ultrasound probe in the plurality of X-ray images.

4. The image processing device according to claim 1, wherein the interventional tool comprises an ultrasound probe, and wherein the at least one target object is the ultrasound probe.

5. The image processing device according to claim 1, wherein each of the plurality of X-ray images is generated by an X-ray imaging device, each of the plurality of ultrasound images is generated by an ultrasound imaging device, and the X-ray imaging device and the ultrasound imaging device are configured to acquire the plurality of X-ray images and the plurality of ultrasound images simultaneously.

6. A method for enhancing ultrasound images for a medical procedure, comprising:
   a) providing a plurality of ultrasound images of a region of interest of an object;
   b) providing a plurality of X-ray images of the region of interest of the object;
   c) selecting at least one target object in one X-ray image of the plurality of X-ray images, wherein the at least one target object is an interventional tool configured to be moved in the region of interest of a patient during the medical procedure;
   d) tracking movement of the at least one target object in other X-ray images of the plurality of X-ray images subsequent to the one X-ray image;
   e) registering the plurality of ultrasound images and the plurality of X-ray images;
   f) detecting the at least one target object in the plurality of ultrasound images based on the tracking of movement of the at least one target object and the registration, wherein the detecting comprises: i) projecting an outline of the at least one target object in the plurality of X-ray images into the plurality of ultrasound images and ii) detecting the at least one target object in the plurality of ultrasound images based on selecting at least one object in the plurality of ultrasound images that fit into the projected outline;
   g) highlighting at least an area of the detected at least one target object in the plurality of ultrasound images there by gene rating a boosted ultrasound image; and
   h) tracking, via the boosted ultrasound image, movement of the at least one target object in the region of interest of the patient during the medical procedure.

7. The method according to claim 6, wherein each of the plurality of X-ray images is generated by an X-ray imaging device, each of the plurality of ultrasound images is generated by an ultrasound imaging device, and the X-ray imaging device and the ultrasound imaging device are configured to acquire the plurality of X-ray images and the plurality of ultrasound images simultaneously.

8. A non-transient, computer readable medium having stored thereon program code which, when executed by a processor, causes operations for enhancing ultrasound images fora medical procedure, the operations comprising:
   a) receiving a plurality of ultrasound images of a region of interest of an object;
   b) receiving a plurality of X-ray images of the region of interest of the object;
   c) selecting at least one target object in one X-ray image of the plurality of X-ray images, wherein the at least one target object is an interventional tool configured to be moved in the region of interest of a patient during the medical procedure;
   d) tracking movement of the at least one target object in other X-ray images of the plurality of X-ray images subsequent to the one X-ray image;
   e) registering the plurality of ultrasound images and the plurality of X-ray images;
   f) detecting the at least one target object in the plurality of ultrasound images based on the tracking of movement of the at least one target object and the registration, wherein the detecting comprises: i) projecting an outline of the at least one target object in the plurality of X-ray images into the plurality of ultrasound images and ii) detecting the at least one target object in the plurality of ultrasound images based on selecting at least one object in the plurality of ultrasound images that fit into the projected outline;
   g) highlighting at least an area of the detected at least one target object in the plurality of ultrasound images thereby generating a boosted ultrasound image; and
   h) tracking, via the boosted ultrasound image, movement of the at least one target object in the region of interest of Hall the patient during the medical procedure.

9. The non-transient, computer readable medium according to claim 8, wherein each of the plurality of X-ray images is generated by an X-ray imaging device, each of the plurality of ultrasound images is generated by an ultrasound imaging device, and the X-ray imaging device and the ultrasound imaging device are configured to acquire the plurality of X-ray images and the plurality of ultrasound images simultaneously.

\* \* \* \* \*